United States Patent
Perron et al.

(10) Patent No.: US 7,485,288 B2
(45) Date of Patent: Feb. 3, 2009

(54) COSMETIC COMPOSITION COMPRISING CALCIUM CARBONATE PARTICLES AND CONDITIONING AGENTS

(75) Inventors: Beatrice Perron, Jouy En Josas (FR); Serge Restle, Saint-Prix (FR); Franck Giroud, Clichy (FR); Henri Samain, Bievres (FR)

(73) Assignee: L'Oreal, Paris (FR)

(*) Notice: Subject to any disclaimer, the term of this patent is extended or adjusted under 35 U.S.C. 154(b) by 719 days.

(21) Appl. No.: 10/479,183

(22) PCT Filed: May 31, 2002

(86) PCT No.: PCT/FR02/01850
§ 371 (c)(1),
(2), (4) Date: May 28, 2004

(87) PCT Pub. No.: WO02/096385
PCT Pub. Date: Dec. 5, 2002

(65) Prior Publication Data
US 2004/0197356 A1    Oct. 7, 2004

(30) Foreign Application Priority Data
May 31, 2001    (FR) .................. 01 07152

(51) Int. Cl.
*A61Q 5/12* (2006.01)
*A61Q 5/00* (2006.01)

(52) U.S. Cl. .............. 424/70.1; 424/70.4; 424/70.12; 424/70.122; 424/70.22; 424/70.27

(58) Field of Classification Search .............. 424/70.1, 424/70.4, 70.12, 70.122, 70.22, 70.27, 70.28
See application file for complete search history.

(56) References Cited

U.S. PATENT DOCUMENTS

| | | | |
|---|---|---|---|
| 3,958,581 A | 5/1976 | Boiteux et al. | |
| 4,895,722 A | 1/1990 | Abe et al. | |
| 4,983,383 A | 1/1991 | Maksimoski et al. | |
| 5,334,376 A | 8/1994 | Robbins et al. | |
| 5,688,808 A | 11/1997 | Jones et al. | |
| 5,696,130 A | 12/1997 | Jones et al. | |
| 5,738,974 A | 4/1998 | Nagasaka et al. | |
| 5,756,076 A * | 5/1998 | Cervantes et al. | 424/70.1 |
| 6,017,924 A | 1/2000 | Edwards et al. | |
| 6,083,956 A | 7/2000 | Gunt | |
| 6,642,038 B1 | 11/2003 | Canfield | |
| 6,667,313 B1 | 12/2003 | Hamann et al. | |
| 2002/0183346 A1 | 12/2002 | Zhi et al. | |
| 2005/0227881 A1 | 10/2005 | Polonka et al. | |

FOREIGN PATENT DOCUMENTS

| | | |
|---|---|---|
| DE | 3824094 | 1/1989 |
| DE | 199 46 784 | 4/2001 |
| DE | 19946784 A1 * | 4/2001 |
| EP | 0 370 764 | 5/1990 |
| EP | 0 399 157 | 11/1990 |
| EP | 0 449 133 | 10/1991 |
| JP | 01 313415 | 12/1989 |
| JP | 11 228332 | 8/1999 |
| WO | 99 25312 | 5/1999 |

OTHER PUBLICATIONS

Flick, E, Cosmetics Additives, 1991, Noyes Publications, p. 233.*
Dickhof, S. et al., "Hair care agent with anti-grease effect", Apr. 19, 2001, DE 19946784, English translation.*
National Starch and Chemical, Celquat L-200, A Sensory Modifer with Hold, Europe: Sempach-Station, Switzerland.

* cited by examiner

*Primary Examiner*—Gina C Yu
(74) *Attorney, Agent, or Firm*—Oblon, Spivak, McClelland, Maier & Neustadt, P.C.

(57) ABSTRACT

The invention concerns a cosmetic composition, in particular for the hair, comprising, in a cosmetically acceptable medium: solid particles containing at least 10 wt. % of carbonate calcium; at least a conditioning agent selected among: (i) cationic surfactants selected among quaternary esters, quaternary diammonium except those derived from diaminopropane, imidazolium and amides, (ii) cationic silicones, and (iii) cationic polymers whereof the cationic charge density is not more than 7 meq/g and, preferably not less than 0.05 meq/g.

17 Claims, No Drawings

COSMETIC COMPOSITION COMPRISING CALCIUM CARBONATE PARTICLES AND CONDITIONING AGENTS

The present invention relates to a cosmetic composition, especially the hair composition, containing, in a cosmetically acceptable medium, calcium carbonate particles and at least one conditioner. The invention is also directed toward a cosmetic hair treatment process comprising the application of this composition, and to its use as a rinse-out hair product.

It is common practice to use detergent hair compositions (or shampoos) based essentially on standard surfactants especially of anionic, nonionic and/or amphoteric type, but more particularly of anionic type, for cleansing and/or washing the hair. These compositions are applied to wet hair and the lather generated by massaging or rubbing with the hands makes it possible, after rinsing with water, to remove the various types of soiling initially present on the hair.

These base compositions do indeed have good washing power, but the intrinsic cosmetic properties associated therewith remain quite poor, especially due to the fact that the relatively aggressive nature of such a cleansing treatment can in the long run result in more or less pronounced damage to the hair fibers, which is associated in particular with the gradual removal of the lipids or proteins contained in them or at their surface.

Thus, to improve the cosmetic properties of the above compositions, and more particularly of those intended to be used on sensitized hair (i.e. hair that is damaged or embrittled especially due to the chemical action of atmospheric agents and/or hair treatments such as permanent-waving, dyeing or bleaching), it is now common practice to introduce into these compositions additional cosmetic agents known as conditioners, which are intended mainly to repair or limit the harmful or adverse effects induced by the various treatments or attacking factors to which the hair fibers are more or less repeatedly subjected. These conditioners may, of course, also improve the cosmetic behavior of natural hair.

The conditioners most commonly used to date in shampoos are cationic polymers, silicones and/or silicone derivatives, which in fact give washed, dry or wet hair markedly increased ease of disentangling and softness when compared with that which may be obtained with the corresponding cleansing compositions from which they are absent.

However, these cosmetic advantages are unfortunately also accompanied, on the dried hair, by certain cosmetic effects that are considered undesirable, i.e. lankness of the hairstyle and a lack of smoothing.

In addition, the use of cationic polymers for this purpose presents various drawbacks. On account of their high affinity for the hair, some of these polymers become deposited in large amount during repeated use, and lead to adverse effects such as an unpleasant, laden feel, stiffening of the hair, and adhesion between the fibers, which affects the styling. These drawbacks are accentuated in the case of fine hair, which lacks liveliness and volume.

It has already been proposed to use particles in rinse-out compositions, so as to improve the feel and appearance of the hair. By weight of illustration, U.S. Pat. No. 5,334,376 proposes the addition of calcium carbonate particles to hair conditioning compositions containing a silicone, a fatty alcohol and an amide.

It has also been proposed, in patent application DE 199 46 784, to use particles of the various oxides, hydroxides, carbonates, silicates or phosphates in hair compositions, to reduce the greasy appearance of the hair. It is generally envisioned to combine these particles with standard shampoo ingredients.

However, despite the progress recently made in the field of rinse-out hair products and especially shampoos, these products are not truly totally satisfactory, and as such there is currently still a strong need for novel products that show better performance qualities as regards one or more of their properties.

The Applicant has discovered, surprisingly and unexpectedly, that by selecting the conditioner, combined with calcium carbonate particles, it is possible to improve the results obtained with cosmetic products, especially rinse-out hair products, in terms of cosmetic properties and shaping properties. In particular, the hair is given texture (increased sensation of thickness) and better hairstyle hold.

One subject of the invention is a cosmetic composition, especially a hair composition, comprising, in a cosmetically acceptable medium:
(a) solid particles containing at least 10% by weight of calcium carbonate;
(b) at least one conditioner chosen from:
   (i) cationic surfactants chosen from quaternary esters, diquaternary ammoniums except for those derived from diaminopropane, imidazoliniums and amides,
   (ii) cationic silicones, and
   (iii) cationic polymers whose cationic charge density is less than or equal to 7 meq/g and preferably greater than or equal to 0.05 meq/g.

Another subject of the present invention consists of a cosmetic hair treatment process using the composition according to the invention.

A subject of the invention is also the use of the cosmetic hair composition especially in rinse-out hair application.

Other subjects, characteristics, aspects and advantages of the invention will emerge even more clearly on reading the description and the various examples that follow.

(a) Calcium Carbonate Particles

The particles containing at least 10% by weight of calcium carbonate preferably have a number-average primary size of between 2 nm and 2 μm, more preferably between 5 and 500 nm and even more preferably between 10 and 250 nm.

The particles according to the invention may be, for example, in any form, for example in the form of spheres, flakes, needles, platelets or totally random forms.

In accordance with the present invention, the particle may be a solid particle formed entirely from calcium carbonate. Calcium carbonate may also totally or partially constitute the core of the particle, this core being coated with another constituent, for instance an oxide, a silicate or a metal. Calcium carbonate may also exclusively form the coating of a substrate of different chemical constitution, for instance an oxide, a silicate or a metal.

For the purposes of the present invention, the expression "primary particle size" means the maximum size that it is possible to measure between two diametrically opposite points on an individual particle. The size may be determined, for example, by transmission electron microscopy or by measuring the specific surface area by the BET method or alternatively using a laser granulometer.

When the particles are formed by calcium carbonate and other fillers, the calcium carbonate is in free form and does not form chemical bonds with the other fillers. It is then a matter of an alloy between the calcium carbonate and other fillers, especially with metal or metalloid oxides, obtained in particular by thermal fusion of these various constituents.

When the particles containing at least 10% by weight of calcium carbonate also comprise a metal or metalloid oxide, this oxide is chosen especially from silicon oxide, boron oxide and aluminum oxide.

Preferably, the particles contain at least 50% by weight of calcium carbonate and better still at least 70% by weight, and particles consisting of more than 90% by weight of calcium carbonate are particularly preferred according to the present invention.

Even more advantageously, the particles containing at least 10% by weight of calcium carbonate are particles of substantially pure calcium carbonate.

The particles containing calcium carbonate according to the invention are used especially in an amount of between 0.01% and 30% by weight and preferably between 0.05% and 5% by weight relative to the total weight of the composition.

The calcium carbonate that is suitable for use in the compositions of the present invention may be of natural origin or may be of synthetic origin. In the latter case, it may be obtained from calcium oxide, calcium peroxide, calcium acetate or calcium ethoxide.

The composition according to the invention may also contain other types of particles, for example titanium oxide, zinc oxide or aluminum oxide particles.

(b) Conditioners

The conditioners that are suitable for use in the present invention are especially the following:

(i) Cationic Surfactants Chosen from Quaternary Esters, Diquaternary Ammoniums, Imidazoliniums and Amides quaternary esters the diquaternary ammonium salts advantageously have the formula (III):

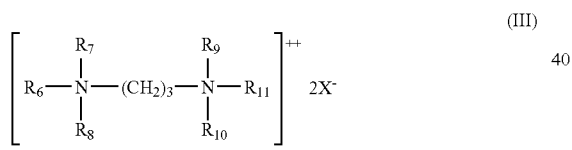

in which $R_6$ denotes an aliphatic radical containing from 16 to 22 carbon atoms, $R_7$, $R_8$, $R_9$, $R_{10}$ and $R_{11}$ are chosen from hydrogen or an alkyl radical containing from 1 to 4 carbon atoms, and $X^-$ is an anion chosen from the group of halides, acetates, phosphates and sulfates.

The diquaternary ammonium salts targeted by the present invention are not diaminopropane derivatives.

the quaternary ammonium salts of imidazolinium advantageously have the formula (II) below:

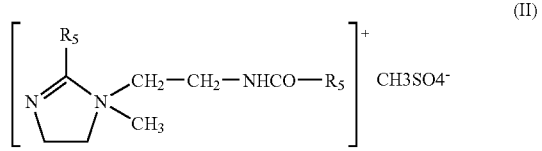

in which $R_5$ represents a mixture of alkenyl and/or alkyl radicals containing from 13 to 21 carbon atoms and tallow fatty acid derivatives.

the amides have the general formula (I) below:

in which the radicals $R_1$ to $R_4$, which may be identical or different, represent an alkylamide radical containing from about 12 to about 22 carbon atoms; X is an anion chosen from the group of halides, phosphates, acetates, lactates, alkyl sulfates, alkyl sulfonates and alkylaryl sulfonates.

(ii) Cationic Silicones

Such cationic silicones especially comprise the polymers of formula (V):

in which

G is chosen from the group formed by H, OH, $C_{1-8}$ alkyl, and phenyl, and preferably denotes methyl, a denotes 0 or an integer ranging from 1 to 3, and is preferably equal to 0, b denotes 0 or 1, and is preferably equal to 1, the sum (n+m) represents an integer ranging from 0 to 2 000 and preferably ranging from 50 to 150, n possibly denoting a number ranging from 0 to 1 999 and preferably ranging from 49 to 149, and m possibly denoting a number ranging from 1 to 2 000 and preferably ranging from 1 to 10, $R_{12}$ is a monovalent radical of formula $C_qH_{2q}L$ in which q=2 to 8, L being chosen from the following groups:

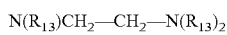

in which $R_{13}$ is chosen from the group formed by H, phenyl, benzyl, a saturated hydrocarbon-based radical, preferably an alkyl radical containing from 1 to 20 carbon atoms, and $A^-$ denotes a halide ion.

These polymers of formula (V) are especially compounds described in the CTFA dictionary under the names "Amodimethicone" and "Trimethylsilyamo-dimethicone".

One amodimethicone that is more particularly preferred here is the product sold under the trade name "Cationic Emulsion DC 939" (or DC 939) by the company Dow Corning, which is a combination of Amodimethicone, of hexadecyltrimethylammonium chloride and of polyoxyethylenated tridecyl alcohol, as an aqueous emulsion containing 36% Amodimethicone.

A trimethylsilylamodimethicone that is more particularly preferred is the product sold by the company Dow Corning under the name "Dow Corning Q2 7224".

Other cationic silicones that may also be used in the composition according to the present invention are polymers of formula (VII):

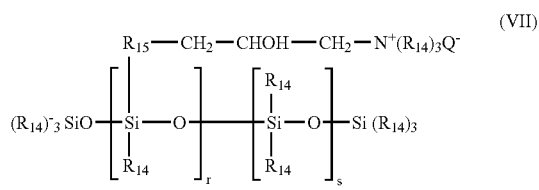

in which $R_{14}$ denotes a hydrocarbon-based radical containing from 1 to 18 carbon atoms, in particular an alkyl or alkenyl radical, and preferably methyl, $R_{15}$ denotes a hydrocarbon-based radical, preferably an alkylene radical containing from 1 to 18 carbon atoms or an alkylenoxy radical containing from 1 to 18 carbon atoms and preferably from 1 to 8 carbon atoms, $Q^{31}$ denotes a halide ion and preferably a chloride ion, r represents a mean statistical value ranging from 2 to 20 and preferably from 2 to 8, s represents a mean statistical value ranging from 20 to 200 and preferably from 20 to 50.

These compounds are described in greater detail in U.S. Pat. No. 4,185,087.

A polymer of this type that is more particularly preferred is the product sold by the company Union Carbide under the name "Ucar Silicone Ale 56".

The cationic silicone is preferably chosen from "Amodimethicone" and "Trimethylsilylamo-dimethicone".

(iii) Cationic Polymers with a Cationic Charge Density of Less than or Equal to 7 meq/g and Preferably Greater than or Equal to 0.05 meq/g The cationic polymers used in accordance with the invention generally have a weight-average molecular weight of at least 5000, preferably of at least 10 000, and less than 10 000 000, and more particularly ranging from 100 000 to 2 000 000. They generally have units containing a nitrogen atom, such as quaternary ammonium or amino units or mixtures thereof. Their cationic charge density is less than or equal to 7 meq/g and preferably greater than or equal to 0.05 meq/g and more preferably between 0.5 and 7 meq/g. The charge density can be determined according to the Kjeldahl method. It generally corresponds to a pH of about 3 to 9.

Among the cationic polymers which can be used according to the invention, mention may be made of copolymers of vinyl monomers having amine or quaternary ammonium functions with water-soluble monomers containing ethylenic unsaturation, such as acrylamide, methacrylamide, alkyl- or dialkyl (meth)acrylamides, alkyl (meth)acrylates, vinylcaprolactone, vinylpyrrolidone; or alternatively other monomers such as vinyl esters, vinyl alcohol, maleic anhydride, propylene glycol, ethylene glycol. The alkyl or dialkyl groups of the amine or ammonium functions are preferably $C_1$-$C_9$ and more preferably $C_1$-$C_3$.

The amines can be primary, secondary or tertiary. Secondary and tertiary amines are preferred.

The amino-substituted vinyl monomers can be polymerized in their amine form and then optionally quaternized. The amines can also be quaternized after formation of the polymer. For example, the tertiary amine functions can be quaternized by reaction with a salt of formula R'X in which R' is a short-chain (preferably $C_1$-$C_7$ and more particularly $C_1$-$C_3$) alkyl radical and X is an anion forming a water-soluble salt with the quaternary ammonium.

Among the vinyl monomers containing amine or quaternary ammonium functions, mention may be made, for example, of vinyl compounds substituted with a group such as dialkylaminoalkyl (meth)acrylate, monoalkyl-aminoalkyl (meth)acrylate; trialkylmethacryloxyalkyl-ammonium salts; diallylic salts of quaternary ammonium; quaternary vinyl monomers having rings bearing nitrogen atoms, such as pyridinium, imidazolium, quaternized pyrrolidone, for instance alkylvinylimidazolium, alkylvinylpyridinium, quaternary alkylvinylpyrrolidone salts. The alkyl portions of these monomers are preferably $C_1$-$C_3$ alkyls and more preferably $C_1$ or $C_2$ alkyls.

Mention may also be made, as amino-substituted vinyl monomers, of dialkylaminoalkyl (meth)acrylates and dialkylaminoalkyl (meth)acrylamides. The alkyl or dialkyl groups are preferably $C_1$-$C_9$ and more preferably $C_1$-$C_3$.

The cationic polymers of the invention can comprise mixtures of vinyl monomers derived from amines and/or of vinyl monomers derived from quaternary ammoniums and/or of other compatible monomers. Mention may be made, by way of example, of:

copolymers of 1-vinylpyrrolidone and of a salt of 1-vinyl-3-methylimidazolium (for example the chloride) (known as Polyquaternium-16 in the CTFA dictionary), such as those sold under the name Luviquat by the company BASF;

copolymers of 1-vinyl-2-pyrrolidone and of dimethylaminoethyl methacrylate (known as Polyquaternium-11 in the CTFA dictionary), such as those sold under the name Gafquat (for example Gafquat 755N) by the company GAF Corporation;

dimethyldiallylammonium chloride homopolymers (Polyquaternium-5 in the CTFA dictionary) and copolymers of acrylamide and of dimethyldiallyl-ammonium chloride (Polyquaternium-7 in the CTFA dictionary), such as those sold under the name Merquat 550 and Merquat S by the company Merck;

mineral acid salts of aminoalkyl esters of homo- and copolymers of unsaturated carboxylic acids having from 3 to 5 carbon atoms, such as those described in U.S. Pat. No. 4,009,256.

Among the cationic polymers that can be used, mention may also be made of cationic polysaccharides such as cationic cellulose derivatives and cationic starch derivatives.

Among the cationic polysaccharides, mention may be made of polymers of formula:

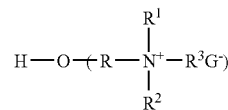

in which:

H is an anhydroglucose residue such as starch or a cellulosic anhydroglucose residue;

R is an alkylene, an oxyalkylene, a polyoxyalkylene or a hydroxyalkylene or mixtures thereof;

$R^1$, $R^2$ and $R^3$, which may be identical or different, denote an alkyl, aryl, alkylaryl, arylalkyl, alkoxyalkyl or alkoxyaryl group; each group containing up to 18 carbon atoms and the total number of carbon atoms per cationic unit is preferably less than or equal to 20;

$G^-$ is an anion resulting from the quaternization of the amine $NR^1R^2R^3$.

Among the cationic cellulose polymers, mention may be made of those sold by the company Amerchol Corp. under the names JR and LR, such as the quaternary hydroxyethylcellulose salts obtained by reaction with an epoxide substituted with a trimethylammonium (Polyquaternium-10 in the CTFA dictionary). Mention may also be made of the quaternary hydroxyethylcellulose salts obtained by reaction with an epoxide substituted with lauryldimethylammonium (Polyquaternium-24 in the CTFA dictionary), such as those sold under the name Polymer LM200 by Amerchol Corp.

As cationic polymers which can be used according to the invention, mention may also be made of cationic guar gum derivatives, such as hydroxypropyltrimonium guar chloride sold under the name Jaguar by the company Celanese Corp.

Mention may also be made of quaternary cellulose ethers, such as those described in U.S. Pat. No. 3,962,418 and etherified copolymers of cellulose and of starch, such as those described in U.S. Pat. No. 3,958,581.

The conditioners of the invention are present in the compositions in proportions preferably ranging from 0.01 to 5% by weight and preferably from 0.1 to 3% by weight relative to the total weight of the composition.

Composition

The cosmetically acceptable medium may consist solely of water or of a mixture of water and one or more cosmetically acceptable solvents, or of one or more cosmetically acceptable solvents, such as a $C_1$-$C_4$ lower alcohol, for instance ethanol, isopropanol, tert-butanol or n-butanol; alkylene glycols, for instance propylene glycol, and glycol ethers.

The detergent compositions according to the invention have a final pH generally of between 3 and 10. Preferably, this pH is between 4 and 8. The pH can be adjusted to the desired value conventionally by adding a base (organic or inorganic) into the composition, for example aqueous ammonia or a primary, secondary or tertiary (poly)amine such as monoethanol-amine, diethanolamine, triethanolamine, isopropanolamine or 1,3-propanediamine, or alternatively by adding an acid, preferably a carboxylic acid such as, for example, citric acid.

The compositions in accordance with the invention can contain, in addition to the combination defined above, viscosity modifiers such as electrolytes, or thickeners (associative or non-associative). Mention may be made in particular of sodium chloride, sodium xylenesulfonate, scleroglucans, xanthan gums, fatty acid alkanolamides, alkanolamides of carboxylic acid alkyl ether optionally oxyethylenated with up to 5 mol of ethylene oxide, such as the product sold under the name "Aminol A15" by the company Chem Y, crosslinked polyacrylic acids and crosslinked acrylic acid/$C_{10}$-$C_{30}$ alkyl acrylate copolymers. These viscosity modifiers are used in the compositions according to the invention in proportions that may range up to 10% by weight relative to the total weight of the composition.

The compositions in accordance with the invention can also contain up to 5% of pearlescent agents or opacifiers that are well known in the state of the art, such as, for example, fatty alcohols greater than C16, acyl derivatives containing a fatty chain, such as monostearates or distearates of ethylene glycol or of polyethylene glycol, fatty-chain ethers such as distearyl ether or 1-(hexadecyloxy)-2-octadecanol.

The compositions in accordance with the invention may also optionally contain at least one additive chosen from foam synergists such as $C_{10}$-$C_{18}$ 1,2-alkanediols or fatty alkanolamides derived from monoethanolamine or from diethanolamine, silicone or nonsilicone sunscreens, surfactants other than those of the invention, anionic, nonionic, cationic or amphoteric polymers, proteins, protein hydrolysates, hydroxy acids, vitamins, provitamins such as panthenol, and volatile or nonvolatile, linear or cyclic, crosslinked or non-crosslinked, organomodified or non-organomodified non-cationic silicones.

Needless to say, a person skilled in the art will take care to select this or these optional additional compound(s) and/or the amounts thereof such that the advantageous properties intrinsically associated with the combination in accordance with the invention are not, or are not substantially, adversely affected by the envisioned addition(s).

These additives are optionally present in the composition according to the invention in proportions that may range from 0.00001% to 20% by weight relative to the total weight of the composition. The precise amount of each additive is readily determined by a person skilled in the art depending on its nature and its function.

These compositions may be in the form of more or less thickened liquids, creams or gels, and they are mainly suitable for washing and caring for keratin materials, in particular the hair and the skin and even more particularly the hair.

When the compositions in accordance with the invention are used as standard shampoos, they are simply applied to wet hair and the lather generated by massaging or friction with the hands is then removed, after an optional leave-in time, by rinsing with water, the operation possibly being repeated one or more times.

A further subject of the invention is a process for washing and conditioning keratin materials such as in particular the hair, which comprises applying a composition as defined hereinabove, then rinsing with water after an optional leave-in time.

The compositions according to the invention are preferably used as shampoos for washing and conditioning the hair, and in this case they are applied to wet hair in amounts that are effective to wash it, this application being followed by rinsing with water.

The compositions in accordance with the invention may also be used as shower gels for washing and conditioning the hair and/or the skin, in which case they are applied to the wet skin and/or hair and are rinsed off after application.

The compositions of the invention may also be used in leave-in mode, and in particular in lotions, gels, mousses or aerosols.

Concrete, but in no way limiting, examples illustrating the invention will now be given.

EXAMPLES

The two compositions below are prepared:

| Shampoo | |
|---|---|
| Triethanolamine lauryl sulfate at a concentration of 40% AM (1) | 31.3% |
| Copolymer (2) | 3.1% |
| Calcium carbonate powder (3) | 3% |
| qs pH = 7 | |
| qs water = 100 | |
| Care | |
| Calcium carbonate powder (3) | 3% |
| Single-chain quaternary ester (4) | 4.5% AM |
| qs pH = 4 | |
| qs water = 100 | |

(1) as an aqueous solution
(2) 8% protected 50/50 dimethyldiallylammonium chloride/acrylamide as an aqueous solution
(3) OmyaPur 3S sold by Omya
(4) behenyloxyhydroxypropyltrimethylammonium chloride at a concentration of 70% in water/hexylene glycol, sold by CHEMY under the name Akypo 131

The composition has a pleasant texture when applied to wet hair. It is easily rinsed out. The wet hair is not laden and is easy to shape.

The invention claimed is:

1. A cosmetic composition, comprising, in a cosmetically acceptable medium:
   one or more solid particles comprising at least 10% by weight of calcium carbonate; and
   at least one conditioner comprising a cationic surfactant selected from the group consisting of quaternary esters and amides.

2. The composition as claimed in claim 1, wherein the particles comprising at least 10% by weight of calcium carbonate have a number-average primary size of between 2 nm and 2 µm.

3. The composition as claimed in claim 1, wherein the solid particles comprise at least 50% by weight of calcium carbonate.

4. The composition as claimed in claim 1, wherein the solid particles are present in an amount of between 0.01% and 30% by weight relative to the total weight of the composition.

5. The composition as claimed in claim 1 wherein the conditioner is present in a proportion of from 0.01% to 5% by weight relative to the total weight of the composition.

6. The composition as claimed in claim 1, comprising one or more amides having the general formula (I) below:

in which the radicals $R_1$ to $R_4$, which may be identical or different, represent an alkylamide radical containing from about 12 to about 22 carbon atoms;

X is an anion chosen selected from the group consisting of halides, phosphates, acetates, lactates, alkyl sulfates, alkyl sulfonates and alkylaryl sulfonates.

7. The composition as claimed in claim 1 further comprising at least one additive selected from the group consisting of foam synergists, silicone sunscreens, nonsilicone sunscreens, surfactants other than those of the invention, anionic polymers, nonionic polymers, cationic polymers, of amphoteric polymers, proteins, protein hydrolysates, hydroxy acids, vitamins, provitamins, panthenol, and volatile or nonvolatile, linear or cyclic, crosslinked or noncrosslinked, organomodified or non-organomodified, non-cationic silicones.

8. A process for washing and conditioning hair, comprising applying an effective amount of a composition as claimed in claim 1 on the hair, and then rinsing with water after an optional leave-in time.

9. The cosmetic composition of claim 1, wherein the cosmetic composition is a hair composition.

10. The composition as claimed in claim 1, wherein the solid particles have a number average primary size of between 5 nm and 500 nm.

11. The composition as claimed in claim 1, wherein the solid particles have a number average primary size of between 10 nm and 250 nm.

12. The composition as claimed in claim 1, wherein the solid particles comprise at least 70% by weight of calcium carbonate.

13. The composition as claimed in claim 1, wherein the solid particles comprise at least 90% by weight of calcium carbonate.

14. The composition as claimed in claim 1, wherein the solid particles are present in an amount of between 0.05% and 5% by weight relative to the total weight of the composition.

15. The composition as claimed in claim 1, wherein the conditioner is present in a proportion of from 0.1% to 3% by weight relative to the total weight of the composition.

16. The composition as claimed in claim 6, wherein the radicals $R_1$ to $R_4$ represent an alkanolamide radical containing from 12 to 22 carbon atoms.

17. A shampoo comprising the cosmetic composition of claim 1.

* * * * *